United States Patent [19]

Hau

[11] Patent Number: 5,981,499
[45] Date of Patent: Nov. 9, 1999

[54] LESION-DIRECTED ANTIBIOTICS IN DRY DOSAGE FORMS FOR THE TREATMENT OF SHALLOW ULCERS OF THE ORAL MUCOSA

[75] Inventor: Kee Hung Hau, Woodbridge, Conn.

[73] Assignee: Atlantic Biomed Corporation, Sint Maarten, Netherlands Antilles

[21] Appl. No.: 09/026,901

[22] Filed: Feb. 20, 1998

[51] Int. Cl.$^6$ .......................... A61K 31/70; A61K 31/65; A61K 33/32; A61K 33/24

[52] U.S. Cl. .............................. 514/29; 514/31; 514/39; 514/152; 514/192; 514/200; 424/641; 424/653; 424/692

[58] Field of Search ................................ 514/29, 31, 39, 514/152, 192, 200; 424/653, 641, 692

[56] References Cited

U.S. PATENT DOCUMENTS

| | | | |
|---|---|---|---|
| 4,177,254 | 12/1979 | Khan et al. ................................ | 424/16 |
| 4,748,022 | 5/1988 | Busciglio ............................. | 424/195.1 |
| 5,049,384 | 9/1991 | Kim ....................................... | 424/405 |
| 5,476,667 | 12/1995 | Kristensen et al. ..................... | 424/489 |
| 5,503,845 | 4/1996 | Goede et al. ............................ | 424/464 |
| 5,534,262 | 7/1996 | Dobrotvorsky et al. ................ | 424/464 |
| 5,637,616 | 6/1997 | Sharpe et al. ........................... | 514/562 |
| 5,679,339 | 10/1997 | Keith et al. ............................. | 424/85.2 |

FOREIGN PATENT DOCUMENTS

| | | |
|---|---|---|
| 743895 | 10/1996 | Canada . |
| 9522983 | 8/1995 | WIPO . |
| 9624342 | 8/1996 | WIPO . |
| 97-02021 | 1/1997 | WIPO . |

OTHER PUBLICATIONS

Spark, R.P., Fatal Anaphylaxis due to oral penicillin, Am. J. Clin. Path. 56, 1971, 407–411.
Chain, E., et al., Penicillin as a chemotherapeutic agent, Lancet 2, 1940, 226–228.
Abraham, E.P., et al., Further observations on penicillin, Lancet 2, 1941, 177–189.
Weinstein, L., Clinical and bacteriologic studies of the . . . gram–negative bacilli, New Eng. J. Med. 271, 1964, 525–532.
Grzesiak, J.J. and Pierschbacher, M.D., Shifts in the concentrations . . . migratory response, J. Clin. Invest. 95, 1995, 227–233.
Drug Information 97, published by Authority of the Board of the American Society of Health–System Pharmacists, 251–252 (1997).
The Dispensatory of the USA, 25th Ed. based on 15th Rev. of US Pharmacopoeia, 10th Ed. of Nat. Formulary, Britsh Pharmacopoeia, 1953, 1st Ed. of Intl. Pharmacopoeia, Vo. I & II, 1955, 1007–1008.
The Use of Antibiotics, edited by A. Kucers and N. Mck. Bennett, 4th Ed., 1987, pp. 16–18.
Osol, et al., (Editors) The Dispensatory of the United States of America, 25th Edition Philadelphia Montreal, J.B. Lippincott Company, Part I, pp. 1006–1008, (1955).

Thoma, et al., Oral Pathology, Fifth Edition, The C.V. Mosby Company, pp. 1066–1069, (1960).
Kucers et al., The Use Of Antibiotics, J.B. Lippincott Company, Fourth Edition, pp. 16–18 (1988).
Gastrointestinal Disease, Fifth Edition, vol. 1, W.B. Saunders Company, p. 273 (1993).
G. Darmstadt et al., "Disorders of the Mucous Membranes," Chapter 614, Nelson Textbook of Pediatrics, 15th ed., W.B. Saunders Company, pp. 1888–1889, (1996).
Goodman and Gilman's The Pharmacological Basis of Therapeutics, 6th ed., Macmillian Publishing Co., Inc., pp. 1136–1137 (1980).
Berkow (Editor), Recurrent Aphthous Stomatitis, The Merck Manual of Diagnosis and Therapy, pp. 1666–1667, 13th Ed., (1977).
L. Yikontiola, "Doxymycine–cyanoacrylate treatment of recurrent aphthous ulcers," Oral Surgery Oral Medicine Oral Pathology, pp. 329–333, (Mar. 1997).
Physicians' Desk Reference, 41 Ed., pp. 1170–1171 (1987).
Physicians' Desk Reference, 52 Ed., pp. 3097–3098 (1998).
The Merck Index, 11th Ed., pp. 894 (1989).
(Medline Abstract), Rattan J., "Sucralfate Suspension as a treatment of Recurrent Aphthous Stomatitis," From J. Itern. Med. 236(3):341–343, Sep. 1994.
(Medline Abstract), Campisi G., "Sucralfate in odontostomatology. Clinical experience," Jun. 1997, From Minerve Stomatol. 46(6):297–305.
(Medline Abstract), Mahdi AB, "Efficacy of Bioadhesive patches in the treatment of recurrent aphthous stomatitis," Sep. 1996, From J. Oral Pathol. Med. 25(8):416–419.
(Medline Abstract), Merchant HW, "Zinc Sulfate Supplementation For Treatment of Recurring Oral Ulcers," May 1977, From South. Med. J. 70(5):559–561.
(Medline Abstract), Agren MS, "Selenium Zinc, Iron and Copper Levels in Serum of Patients with Arterial and Venous Leg Ulcers," 1986, From Acta Derm Venereol 66(3):237–240.
(Medline Abstract), Slomiany BL, "Sucralfate affects the susceptibility of Helicobacter Pylori to Antimicrobial Agents," 1995, From Scand J. Gastroenterol Suppl. 210:82–84.

(List continued on next page.)

Primary Examiner—Kevin E. Weddington
Attorney, Agent, or Firm—Nash & Titus, LLC

[57] ABSTRACT

The invention provides a medicament for topically treating aphthous ulcers in the oral mucosa, and methods of use. The medicament comprises a troche or powder comprising a dry dosage of one or more antibiotics and, preferably, one or more polyvalent metal compounds. The troche or powder is directly applied to the aphthous ulcer and dissolves in saliva, within about 5 to about 15 minutes, thereby directly delivering a supratherapeutic dosage of the antibiotic to the ulcerated oral tissue. Further, in a preferred embodiment the troche/powder directly delivers a therapeutically high concentration of a polyvalent metal compound in suspension to the aphthous ulcer, thereby forming a protective barrier over the ulcerated oral tissue.

44 Claims, No Drawings

OTHER PUBLICATIONS (Medline Abstract), al–Assi Mt, "Clarithromycin, Tetracycline, and Bismuth: A New Non–Metronidazole Therapy for Helicobacter Pylori Infection," Aug. 1989, From Am. J. Gastroenterol 89(8):1203–05.

(Medline Abstract), Endre L., "Recurrent aphthous ulceration with zinc deficiency and cellular immune deficiency," Nov. 72, From Oral. Surg. Oral. Med. Oral. Pathol. 72(5):559–561.

(Medline Abstract), Greer RO Jr., "A double–blind study of topically applied 5% amlexanox in the treatment of aphthous ulcers," Mar. 1993, From J. Oral. Maxillofac Surg. 51(3):243–248.

(Medline Abstract), Phelan JA, "Major aphthous–like ulcers in patients with AIDS," Jan. 1991, From Oral Surg. Oral Med. Oral Pathol. 71(1):68–72.

(Medline Abstract), Sunairi M., "Effect of anti–ulcer agents on antibiotic activity against Helicobacter pylori," Dec. 1994, From Eur. J. Gastroenterol Hepatol 6 Suppl. 1:S121–S124.

(Medline Abstract), Grzesiak JJ, "Changes in the concentrations of extracellular Mg++ and Ca++ dow–regulate E–cadherin and up–rejulate . . . ," May 1995, From J. Invest Dermatol 104(5):768–774.

(Medline Abstract), Rosch W, "Therapy of peptic ulcer and chronic gastritis with bismuth salts," Sep. 1987, From Z. Gastroenterol 25 Suppl. 4:34–40.

(Medline Abstract), Cox RD, "Evaluation of intravenous magnesium sulfate for the treatment of hydrofluoric acid burns", 1994, From J. Toxicol Clin. Toxicol 32(2):123–126.

(Medline Abstract), Harris JC, "Comparative efficacy of injectable calcium and magnesium salts in the therapy of hydrofluoric acid burns," Sep. 1981, From Clin. Toxicol. 18(9):1027–1032.

(Medline Abstract), Jacobson JM, "Thalidomide for the treatment of oral aphthous ulcers in patients with human immunodeficiency virus infections . . . ," May 22, 1997, From N. Engl. J. Med. 336(21):1487–1493.

Grzesiak et al., "Shifts in the Concentrations . . . Migratory Response," J. Clin. Invest., vol. 95, pp. 227–233 (1995).

Tone et al., "Influence of Zinc Deficiency on Phagocytosis in Mice," Kitasato Arch. of Exp. Med., vol. 64, No. 4, pp. 263–269 (1991).

LESION-DIRECTED ANTIBIOTICS IN DRY DOSAGE FORMS FOR THE TREATMENT OF SHALLOW ULCERS OF THE ORAL MUCOSA

BACKGROUND OF THE INVENTION

1. Field of the Invention

Small shallow painful mucosal ulcers of the mouth, commonly referred to as aphthous stomatitis, aphthous ulcers or canker sores in the medical literature, occur in about 25% of the general human population and are not contagious. They often appear on the unkeratinized oral mucosal surface of the soft palate, the ventral or lateral tongue, the buccal-labial mucosa, and the floor of the mouth, and usually recur at irregular intervals. They are often covered with a grayish white exudate and surrounded by a hyperemic or erythematous margin, and are highly sensitive, especially to acid food. The size of these ulcers is rarely more than 5 mm in diameter, but can be larger, and coalescence of multiple ulcers may occur. The pain caused by these ulcers may extend over the entire face. Small aphthous ulcers usually heal spontaneously in one to three weeks, but larger ulcers may require months to resolve, often with scarring.

Although aphthous ulcers were described by Hippocrates, the etiology of these lesions is still largely unknown. While a variety of conditions are associated with aphthous ulcers, immunologic status seems to be an important factor in initiating eruptions. For example, aphthous-like ulcers are often associated with allergic reactions, human immunodeficiency virus and herpes simplex infection. In some patients, the incidence of ulcer formation correlates with menstrual cycles. In other cases dietary or digestive disturbances seem to be the precipitating factors. Prolonged fever, emotional stress, local trauma, low serum iron, ferritin or zinc levels, deficiency of vitamin $B_{12}$ or folate, malabsorption in association with celiac or Crohn's disease, food hypersensitivity and drug reactions may also promote aphthous ulcers.

The first stage of an emerging canker is a vesicle in the stratum granulosum of the mucosal squamous epithelium, produced by intraepithelial edema. The vesicle contains serum and degenerated epithelial cells, with little inflammatory response. This stage is rarely noticed, as the painful symptoms of the ulcer do not occur until the vesicle breaks, presenting an area of ulceration which disrupts the normal epithelium of the mucosa. Once an ulcer forms, the mucosa is no longer protected by an intact epithelium and the raw surface of the ulcer is exposed to microorganisms which normally inhabit the oral cavity.

Examples of indigenous oral flora include lactobacilli, actinomyces, leptotrichiae, α-hemolytic streptococci, enterococci, gram-positive cocci, Neisseriae, diphtheroid bacilli, fusiform bacilli, bacteroides, spirochetes, yeasts and Candida. When existent in normally balanced proportions, these microorganisms do not usually produce disease in the intact oral mucosa of a healthy person. However, upon rupture of a canker ulcer, opportunistic pathogens quickly destroy the remnants of the local surface barrier of the oral mucosa. The result is a secondary infection, characterized by a dense acute and a chronic inflammatory cell infiltration of the exposed connective tissue of the lamina propria mucosae at the crater of the ulcer. The necrotic tissue, fibrinous exudate and the inflammatory cells constitute a yellowish-white membrane often seen clinically covering the base of an ulcer.

Marked infiltration of the small neurovascular system occurs in the deeper layer of the lamina propria mucosae and at the periphery of the ulcer, which may account for the highly sensitive condition of the lesion and pain-inducing neuritis. The process of healing takes place only after the inflammation subsides, and is characterized by re-epithelialization of the ulcer, with or without scarring.

Despite the multifactorial etiology of aphthous ulcers, secondary infections arise after rupture of the intraepithelial vesicle during the early development of all cankers. Control of infection is essential for promoting the healing process. The diverse indigenous flora in the oral cavity possess a range of sensitivities to the chemotherapeutics of choice for the treatment of aphthous ulcers. During an ulcerative infection, stasis of key opportunistic pathogens can inhibit the growth of other dependent microbes, such that the group ceases to function as the causative agent for the infection.

An obstacle to inhibiting microbial proliferation is the fact that many bacteria are resistant to the concentrations of antibiotics attainable in blood or in tissues during medication. This property of drug resistance may be natural or acquired. However, the growth of many "resistant" microorganisms can be inhibited in vitro by increasing the concentrations of the antibiotic to a supratherapeutic level that is not safely attainable in blood or in tissue fluids via conventional gastrointestinal absorption or intramuscular and intravenous injections. For example, Gram-negative bacilli are generally regarded as being resistant to penicillin G, even at the concentration of 16 mcg/ml which is accepted as the average peak blood level after an intravenous injection of 500 mg of penicillin G. However, if a high concentration of penicillin G is used (such as, for instance, 740 mcg/ml) as the cut-off minimum inhibition concentration (MIC) for classifying sensitive and resistant strains, many Gram-negative bacilli (including, for instance, Salmonella, Shigella, most *Escherichia coli* strains, all *Proteus mirabilis* strains and most Bacteroides strains) would fall into the "sensitive" category. Needless to say, in clinical practice, drug toxicity and rapid renal clearance usually prevent this substantial level of antibiotic being achieved in human blood and tissue fluids via systemic oral or parenteral medication.

2. Description of Related Art

The treatment of aphthous stomatitis to date has been palliative, using various measures to lessen the pain, to control secondary infection, and to reduce inflammatory reaction after the painful ulcer is established. The treatments of choice for aphthous ulcers have varied over the years, but in general, palliative treatments have met with only limited success.

For example, in the 1950s, a recommended local treatment of infections of the oral cavity was lozenges of penicillin. The lozenges were prepared by compression of a mixture of amorphous penicillin or benzylpenicillin and dry granules of sucrose, lactose, or a mixture of the two, and suitable binding agents. Each lozenge weighed about 1 gram and contained not less than 90.0% of the prescribed or stated number of Units of penicillin, usually about 1000 Units (an equivalent of 0.625 mg of penicillin G) each. The lozenges were designed to disintegrate slowly, releasing penicillin over a period of 45 to 60 minutes, after which another lozenge was inserted, with this process continuing for 24 hours, except during meals. Adverse reactions included stomatitis upon treatment for more than two days, and a yellowish-brown to black discoloration of the tongue.

However, this topical treatment of aphthous ulcers with penicillin lozenges proved ineffective and was abandoned.

Furthermore, as recently as 1980, the use of penicillin for topical applications to mucous membranes and skin was not advised, as such applications were described as ineffective and likely to produce hypersensitivity. (See "The Pharmacological Basis of Therapeutics", Eds. Gilman Goodman, and Gilman, p.1136.) As a result, this type of treatment for aphthous stomatitis was not included in later teachings.

Treatments for canker ulcers currently include a potent glucocorticoid ointment mixed with an equal volume of Orabase™ (active ingredient: mineral oil; available from Bristol-Myers Squibb of Canada), analgesics, topical anesthetics, such as viscous lidocaine hydrochloride, and various hygienic antiseptic mouth rinses. Systemic therapy with corticosteroids, colchicine, or dapsone in severe cases may be indicated. However, potent glucocorticoid ointments and systemic therapy with corticosteroids are known to be immunosuppressive, leaving patients vulnerable to complications, such as severe systemic bacterial or fungal infections. Thalidomide therapy for oral aphthous ulcers is effective in some HIV-infected patients, though the adverse effects of this teratogenic drug limit its usefulness in general. Topical treatment with tetracycline suspensions or nystatin suspensions, as well as systemic therapy with penicillin, are commonly employed. A drawback to oral antimicrobial rinses and suspensions is their inability to present high enough (supratherapeutic) concentrations of the active drugs in the immediate vicinity of the ulcers to suppress the growth of the pathogens which have contributed to and continue to perpetuate the infection. For example, one protocol requires patients to hold 250 mg of tetracycline in 5–10 mg/ml suspension in the mouth for 2 to 5 minutes to coat the ulcers, then suggests swallowing the remaining liquid. This treatment is often impractical, especially for use in children. Tetracycline oral suspensions are available commercially in concentrations from about 5 mg/ml to about 10 mg/ml. Supratherapeutic concentrations of, for example, 500 mg/ml are not achievable with these solutions. Likewise, topical combination treatments utilizing pastes of crushed tetracycline tablets (150 mg in 1 ml of saline) and tissue adhesive agents, such as cyanoacrylate, cannot achieve such high levels of antibiotic. Besides, this type of treatment must be performed by a dentist.

Some patients with recurrent aphthous stomatitis have responded to therapy with metal salts, such as zinc sulfate or the aluminum subsalt of sucrose-8-sulfate (sucralfate). Combinations of metal salts with antibiotics have proven effective for treating some forms of ulcers, such as gastrointestinal ulcers generated by, for example, *Helicobacter pylori*. Protective bioadhesive hydrogel patches made of cellulose have been used to abate oral ulcer pain and reduce healing time, but the patches alone do not address the infectious component of aphthous stomatitis. Therefore, these recommended treatments do not sufficiently meet the needs of many patients with aphthous ulcers.

SUMMARY OF THE INVENTION

With the above in mind, an object of this invention is to provide an effective topical treatment for shallow aphthous ulcers in the oral mucosa. This is achieved by a novel medicament in the form of a powder, or preferably, a troche.

The troche or powder includes a dry dosage of an antibiotic which, when applied topically, delivers directly to the ulcer a supratherapeutic level of antibiotic, that is, a dosage of the antibiotic which is substantially higher than dosage levels achieved when the antibiotic is delivered to the ulcer through blood by conventional gastrointestinal absorption, intramuscular or intravenous injection of the antibiotic. Thus, the medicament addresses the problems presented by previous canker sore remedies. The antibiotic may be one of the known penicillins, beta-lactam antibiotics, tetracyclines, aminoglycosides, cephalosporins, macrolides, vancomycin, bacitracin, chloramphenicol and their salts and mixtures thereof.

Preferably, the troche or powder includes an effective amount of a salt or oxide of a polyvalent metal compounds such as magnesium, zinc, calcium, aluminum, bismuth, titanium and copper and mixtures thereof. Ideally, the polyvalent metal compound is delivered to the ulcer in a concentration sufficiently high that, when the troche or powder is dissolved in saliva at the site of the ulcer, it forms a protective barrier over the raw surface of the aphthous ulcer.

Along these lines, another object of the invention provides a method of treating shallow aphthous ulcers in the oral mucosa comprising directly topically administering one or both of the above-described troche or powder containing a dry dosage of antibiotic, or preferably, a composition containing antibiotic and polyvalent metal ions.

Another object of the invention is to provide a method for directly creating a protective barrier over the raw surface of an aphthous ulcer, wherein a polyvalent metal compound is directly delivered to the ulcer from a troche or powder, and wherein said polyvalent metal compound forms a protective barrier covering.

These and other objects of the invention will be further characterized in the detailed description of the invention provided hereinafter.

DETAILED DESCRIPTION OF THE INVENTION

As mentioned above, this invention relates to a dry dosage of a topical aphthous ulcer medication in the form of a troche or powder comprising a supratherapeutically high dosage of one or more antibiotics. Preferably, the troche or powder also includes one or more polyvalent metal compounds. Other compounds may be included, such as inactive binding agents, which do not significantly interfere with the effectiveness or activity of the antibiotic. With the troche or powder, it is now possible to provide a method for delivering a dry and supratherapeutical dosage of antibiotics directly to the ulcerated mucosa of an aphthous ulcer.

The troche form of the invention is preferable over the powder, as it is easier to directly apply antibiotic in concentrated levels to an ulcer.

Oral high dosage pellets of therapeutic agents are known in the art, and are disclosed in U.S. Pat. No. 5,476,667 to Kristensen et al., and U.S. Pat. No. 5,503,845 to Goede et al. Orally administrable antibiotics are also well known in the art, disclosed as granules in U.S. Pat. No. 4,177,254 to Khan et al., and as capsules and lozenges in U.S. Pat. No. 5,049,384 to Kim. All of these antibiotic medications are designed for gastrointestinal absorption. The contents of the aforementioned are incorporated by reference herein in their entirety.

The invention provides for a dry dosage form of antibiotics, wherein the dry form of ulcer medication is composed of fine medicinal powders of one or more antibiotics, which may be compressed as troches or kept in powder form. The antibiotic may be any of the antimicrobial agents produced by fungi, bacteria, plants, by chemical synthesis, or by genetic engineering technology, which have bactericidal or bacteriostatic activities in aqueous solutions against opportunistic flora of the human oral cavity. The antimicrobial agent must act without adverse effects on human tissues, and must not impair tissue regeneration. Preferably, the antibiotic selected should be devoid of offensive taste or odor. The antibiotic comprises a member selected from the group consisting of the penicillins, beta-lactam antibiotics, tetracyclines, aminoglycosides, cephalosporins, macrolides, vancomycin, bacitracin, chloramphenicol and their salts. Preferably, the antibiotic is a penicillin. Another preferred antibiotic is a tetracycline.

The troche and powder of this invention are chiefly composed of a pure, active crystalline powder of at least one antibiotic, thereby facilitating delivery of the highest possible concentration of the antimicrobial agent(s) to a canker. To initiate treatment, a troche or small amount of powder containing (for instance, preferably between about 10–200 mg, and most preferably about 50 mg) of antibiotics may be mechanically placed in contact with an aphthous ulcer of the oral mucosa. The troche or powder may be mechanically directed in place, for example, by the fingers. Once in contact with the aphthous ulcer, the troche or powder may be held in position by the tongue, permitting the troche or powder to completely dissolve in saliva, ideally in about 5 to about 15 minutes. The direct release of the contents of the troche or powder to the ulcerated oral mucosa creates an extraordinarily high (that is, a supratherapeutic) level of antibiotic concentration at the base of the ulcer. Thus, unlike previous liquid or tablet therapies for cankers, which utilized moderate amounts of antibiotics intended to be swallowed at some point, the invention provides a unique approach to treating aphthous ulcers, comprising a local oral treatment with a high concentration of dry therapeutic agents in a troche or powder form.

By creating a supratherapeutically high level of antibiotic on the surface of the ulcer, the extraordinarily high concentration gradient favors diffusion of the water-soluble antibiotic molecules through the membrane covering the ulcer into the deeper inflamed tissues to reach a concentration there that is substantially higher than the antibiotic levels that can be achieved via the blood stream by the conventional gastrointestinal absorption or by parenteral injections. Preferably, the troche or powder, when dissolved in saliva at the site of the ulcer, at peak level directly delivers at least about 400 mg antibiotic per 1 ml of saliva, and maintains a topical antibiotic activity for at least about 1 hour, and preferably at a concentration of at least about 2.5 mg antibiotic per 1 ml of saliva.

For instance, where the antibiotic is penicillin, the initial peak concentration of penicillin in saliva at the site of the ulcer may be about 800,000 Units per 1 ml saliva, and the local trough concentration of penicillin in saliva at the site of the ulcer may be about 4,000 Units per 1 ml saliva for about 1 hour. Where the antibiotic is oxytetracycline hydrochloride, the initial peak concentration of oxytetracycline hydrochloride in saliva at the site of the ulcer may be between about 400–800 mg per 1 ml saliva, and the local trough concentration of oxytetracycline hydrochloride in saliva at the site of the ulcer may be about 8 mg per 1 ml saliva for about 1 hour.

Preferably, the antibiotic troche/powder contains an effective amount of one or more innocuous polyvalent metal compounds. Some polyvalent compounds are used in the pharmaceutical arts as lubricants for making oral tablets, as disclosed, for instance, in U.S. Pat. No. 5,534,262 to Dobrotvorsky et al. However, upon release from the invention, polyvalent metal compounds form a protective barrier at the base of the aphthous ulcer. In addition to forming a physical barrier by which it protects the ulcerated tissue, the polyvalent metal ion released from the polyvalent metal compound also promotes the healing of the ulcerated tissue by inducing the migration and phagocytic activity of various cell types integral in wound healing. For example, macrophages, fibroblasts and endothelial cells recruited by metal ions to the injured oral tissue phagocytize invading microbes, establish extracellular matrices, and promote neovascular formation. These known principles are disclosed in, for example, J. Clin. Invest. (1995), 95(1): 227–233 and Kitasato Arch. Exp. Med. (1991), 64(4) :263–269, the contents of which are incorporated by reference herein in their entirety.

The polyvalent metal compound comprises a salt or an oxide of a member selected from the group of metals consisting of magnesium, zinc, calcium bismuth, aluminum, titanium and copper. Preferably, the polyvalent metal compound is a fatty acid salt of a metal, such as a stearate, citrate, benzoate, chloride or a sulfate, or other organic or inorganic acid salt. More preferably, the polyvalent metal compound is a fatty acid salt of magnesium or zinc. The metal compound may be an oxide, although the latter is generally more irritating to the normal oral mucosa than are fatty acid salts.

As mentioned above, the polyvalent metal compound is preferably delivered in a concentration sufficiently high that, when the troche or powder is dissolved in saliva at the site of the ulcer, it forms a protective barrier over the ulcer. This is best accomplished when the metal compound is delivered to the site of the ulcer in a concentration of between about 2–50 mg (preferably 10 mg) per 1 ml of saliva. To that end, it is preferred that the amount of polyvalent metal compound in the troche or powder is between about 0.2–5 mg. Most preferably the polyvalent metal compound is magnesium stearate, present in a range of about 0.5 to about 2.0 mg. Higher concentrations of magnesium stearate may be used, but such levels are prone to irritating the oral mucosa. The polyvalent metal compound, upon release from a troche or powder contacting an aphthous ulcer, achieves a suspended concentration of about 10 mg/ml in saliva. Magnesium stearate and zinc stearate have been used in skin dusting powders, for they are not "wetted" by moisture, and permit seepage and evaporation. In the current invention, magnesium stearate is chosen as an agent to form a protective membrane on the surface of the ulcer while permitting easy diffusion of antibiotics into the inflamed tissues.

In one preferred embodiment, the antibiotic is a penicillin and the polyvalent metal compound is magnesium stearate. In such a case, preferably the amount of penicillin in the troche or powder is about 50 mg and the amount of magnesium stearate is about 1.0 mg.

In another preferred embodiment, the antibiotic is a tetracycline and the polyvalent metal compound is magnesium stearate. Here, preferably the amount of tetracycline in the troche or powder is about 50 mg and the amount of magnesium stearate is about 1.0 mg.

The invention may also include inactive binding agents conventionally used in pharmaceutical formulations. Examples include polymeric binding agents, such as methyl cellulose, ethyl cellulose and hydroxycellulose. Other examples include synthetic polymers, such as polyvinylpyrrolidone, gums, starches, lactose, sucrose and other binding agents commonly known in the art.

The invention is preferably administered four times daily after meals and prior to bedtime. Thorough tooth cleaning is advised prior to introduction of the troche or powder to the aphthous ulcer. When the invention is applied properly as described, the painful sensation of the aphthous ulcer will markedly reduce in 24 hours and disappear in about two days, and the canker heals in about two to about four days, instead of the usual course of about one to about three weeks, or longer.

The invention will become more apparent in the following non limiting examples.

EXAMPLES

TABLE 1

Production and Use of Penicillin/Magnesium Stearate Troches

| Compound | |
|---|---|
| Penicillin G or penicillin V potassium salt (80,000 Units) | 50.0 mg |
| Magnesium stearate | 1.0 mg |
| Stearic acid | 0.6 mg |
| Lactose | 7.5 mg |
| Polyvinylpyrrolidone, cellulose esters and starch binding agents | Balance |
| Total weight | 73.0 mg |
| pH in ddH$_2$O | 6.8–7.2 |

Table 1 shows the reagents combined to make penicillin/magnesium stearate troches. The reagents were mixed in the listed proportion in powder form, with an adequate amount of moisture added to permit standard pharmaceutical compression of the composition into troches weighing about 73 mg. Sample troches selected at random were crushed and suspended in 2 ml of double-distilled water, yielding a neutral acidity of pH 6.8–7.2. Upon placement in a stationary location of the human oral cavity, each therapeutic troche should completely disintegrate in saliva within about 10 to about 15 minutes without causing desquamative injuries or erosion to the intact oral mucosa.

Patients with aphthous ulcers were advised to brush their teeth to rid them of food residues, and to rinse their mouths with water prior to initiating treatment.

One penicillin/magnesium stearate troche was placed in the patients' mouths directly over the ulcerated lesion. The troche was dissolved or disintegrated in a minimum amount of saliva directly over the ulcer in no more than 15 minutes, preferably in about 8 to about 12 minutes. The patients were advised to keep the ingredients of the disintegrated troche at the site of the lesion as long as possible. Food and beverages were avoided for one hour after each treatment. If multiple aphthous ulcers were present, one troche was required for the treatment of each ulcer. The topical treatments were conducted 4 times daily, for example, after breakfast, after lunch, after dinner and before bed time for no more than 4 days. During the first application, some patients felt a slight burning sensation over the ulcer, as the raw ulcers were not protected from irritation. The burning sensation lessened with subsequent applications. The painful symptoms markedly improved after 24 hours. Treated ulcers displayed visible signs of healing within 2 days.

For instance, the first sign of healing is usually the fading of the hyperemic zone at the periphery of the ulcer and the lessening of edema at the base of the ulcer. The membrane covering the ulcer becomes thinner, more translucent, more pearly white instead of a grayish-yellowish white prior to the application and contract with the troche. This process of healing can be observed within 24–48 hours after the first medication, and continues until the whitish membrane sloughs off completely and replaced by the newly regenerating mucosa directly underneath. The size of the ulcer reduces simultaneously.

But the major healing process takes place underneath the membrane at the base of the ulcer. After 4 days of penicillin medication, usually only remnants of a thin pearly whitish membrane remain, if any, covering an incompletely re-epithelialized newly healed ulcer. Also, there was no observed adverse reactions of stomatitis or discoloration of the tongue.

Bacterial counts in the saliva taken from the oral cavity of five patients in the vicinity of the ulcer were conducted. Saliva samples of 10 microliters were pipetted immediately before and 24 hours instituting penicillin troche medication, and each sample was spread on the surface of a 10-cm blood agar Petri dish. The inoculated plates were incubated anaerobically at 37° C. and observed at 18 and 42 hours. The plates inoculated with samples taken before treatment always showed numerous bacterial colonies, ranging from 50 to more than 300 in number, including Neisseriae, Bacteroides, Fusibacteria, *Streptococcus viradans,* Diphtheroids, Non-group A Streptococci, *Proteus mirabilis,* and *Staphylococcus aureas.* After 24 hours of penicillin medication, no bacterial colonies, except occasional yeast-form fungal colonies, were observed after incubation, indicating a total inhibition of the opportunistic pathogenic bacteria in the saliva of the patients under the medication of supratherapeutic dosage of penicillin.

Application of the penicillin/magnesium stearate troches in the aforementioned manner created a supratherapeutic concentration of penicillin on the raw surface of the apthhous ulcer. Assuming that the troche is dissolved in 0.1 ml of saliva locally at the ulcer, the initial concentration of penicillin would reach up to 500 mg/ml, and that of magnesium stearate 10 mg/ml. Under the influence of this extraordinarily high concentration of penicillin G or penicillin V, most microorganisms of the normal flora cannot survive or continue to multiply, permitting tissue regeneration processes to occur under the protective barrier coating formed by the magnesium stearate.

The local concentration of penicillin in the saliva was determined as follows.

One troche containing 50 mg of penicillin G was placed in the sulcus between the lower gum and the buccal mucosa of the patient to be dissolved in a minimum amount of saliva. This loculated pocket of saliva was not swallowed and was not to be diluted with excess saliva from other parts of the mouth for one hour. Two samples were taken for assay to determine the peak and trough local concentrations of penicillin during the one-hour duration of medicinal treatment. At the time when the troche was completely dissolved and one hour later, aliquots of 10 microliters were pipetted from this pocket of saliva solution at the site of medication, representing the peak level and the trough level of antibiotic concentration, and transferred into 10 ml of distilled water to make a 1:1.000 dilution and into 1 ml of distilled water to make a 1:100 dilution, respectively. The diluted saliva antibiotic solutions were passed through a sterile bacteria-filter to remove any bacterial or fungal contaminants of the oral flora.

For determination of the peak concentration, 1 ml of the bacteria-free filtrate was further diluted with 9 ml of nutrient broth to achieve a 1:10,000 dilution of the saliva. Then a serial two-fold dilution was made of this 1:10,000 diluted saliva sample with an equal volume of nutrient broth in a roll of test tubes to obtain a series of 1 ml aliquots of nutrient broth in which the saliva was diluted to 20,000, 40,000, 80,000, 160,000, 320,000, 640,000, 1,280,000 and 2,560,000 folds respectively. One ml of nutrient broth which had been freshly inoculated with a young culture of a standard strain of Staphylococcus aureus (ATCC 29213) having a known minimum inhibitory concentration (MIC) at the range of 0.25–2 units of penicillin/ml was added to each test tube. Thus the final dilutions of the saliva sample were in the range of 40,000 to 5,120,000 folds.

For determining the trough concentration, the entire 1 ml of the 1:100 diluted saliva filtrate was used to make the serial dilutions so that the final dilutions of saliva sample were in the range of 4,000 to 256,000 folds in the final test culture.

As control standards, a series of test tubes containing 1 ml of nutrient broth with varying concentrations of penicillin G potassium salt ranging from 0.1 units to 10 units/ml were similarly mixed with an equal volume of nutrient broth freshly inoculated with the standard tubes of Staphylococcus aureus. Both the test and control standard tubes were incubated at 37° C. for 18 hours. Among the test tubes showing no gross evidence of bacterial growth, the one containing the highest dilution of saliva and the one containing the least amount of penicillin G were considered as having the identical concentration of penicillin, i.e. the MIC of the staphylococcus aureus.

In three experiments conducted as described above, the MIC of penicillin G for the standard strain of Staphylococcus aureus (ATCC 29213) was found consistently to be at 1 unit/ml. The maximum final dilutions of the saliva in nutrient broth in which the bacteria failed to show growth were found to be 1/640,000, 1/1,280,000 and 1/640,000 for the peak concentration samples, and to be 1/4,000, 1/16,000 and 1/64,000 for the trough concentration, respectively. Therefore, it was concluded that the initial peak local concentration of penicillin, although the antibiotic might not be in a strict solution form, had reached 640,000–1,280,000 units/ml in the saliva at the site of topical medication when the troche was allowed to dissolve in a loculated pocket of saliva directly over the canker sore, or about 800,000 units/ml, equivalent to 500 mg/ml of penicillin G. Since a troche contains 50 mg of penicillin, it may be deduced that the troche was dissolved in about 0.1 ml of saliva at the time of its complete dissolution. At the end of the one-hour medicinal treatment duration, the concentration of penicillin was markedly reduced to a low level of 4,000–64,000 units/ml, or 2.5–40 mg/ml. This variation of results was probably due to uncontrollable dilution factors in the oral cavity in the test subjects or due to different rates of drug degradation in different individual's mouths.

In comparison, after a single dose of intravenous injection of penicillin G, usually 500 mg in medical practice as reported in the literature, the average peak blood level is about 16 mcg/ml, or about 26 units/ml. Injecting higher doses may be hazardous and will not increase the blood or the tissue levels because of rapid clearance by the kidneys. Therefore, it is theoretically impossible to deliver a penicillin to the oral mucosa at a concentration of even 100 units/ml via the standard forms of medication through gastrointestinal absorption, intramuscular injection or intravenous injection.

Thus, it is concluded that administering a 50 mg penicillin troche as described in this invention as a topical medication for the treatment of canker sores can produce at the site of the lesion a local peak concentration of penicillins of about 800,000 units/ml, or 500 mg/ml, and a local trough concentration of about 4,000 units/ml, or 2.5 mg/ml. This level of antibiotic concentration which can be maintained for at least one hour is about 150 to 30,000 times the highest blood level that can be achieved by the conventional routes of medication via gastrointestinal absorption, or intramuscular or intravenous injections.

EXAMPLE II

TABLE 2

Production and Use of Oxytetracycline Hydrochloride/Magnesium Stearate Troches

| Compound | |
|---|---|
| Oxytetracycline hydrochloride | 50.0 mg |
| Magnesium stearate | 1.0 mg |
| Stearic acid | 0.6 mg |
| Lactose | 7.5 mg |
| Polyvinylpyrrolidone, cellulose esters and starch binding agents | Balance |
| Total weight | 73.0 mg |
| pH in ddH$_2$O | 6.8–7.2 |

Table 2 shows the reagents used to synthesize oxytetracycline/magnesium stearate troches. The oxytetracycline hydrochloride troches were prepared as described in Example 1. These troches were designed for patients with allergies to penicillins.

When the oxytetracycline hydrochloride/magnesium stearate troches are applied in the manner described in Example 1, extraordinarily high concentrations of antibiotic were released on the raw surface of the treated ulcers. Assuming that the troche is dissolved in 0.1 ml of saliva, the peak concentration of oxytetracycline would be between about 400–800 mg/ml locally at the site of the ulcer, and that of magnesium stearate 10 mg/ml.

A similar experiment to the one described in Example I was designed and conducted in two subjects to test the initial peak concentration and the one-hour trough concentration of oxytetracycline hydrochloride in the loculated pocket of saliva after a troche containing 50 mg of the antibiotic was grossly dissolved in the sulcus between the lower gum and the buccal mucosa. The final concentrations of oxytetracycline in the control standard nutrient broth were 0.25 mcg/ml, 0.5 mcg/ml, 1.0 mcg/ml, 2.0 mcg/ml, 4.0 mcg/ml, and 8.0 mcg/ml. The final dilutions of saliva sample were 1/50,000, 1/100,000, 1/200,000, 1/400,000, 1/800,000 and 1/1,600,000 for the peak concentration test tubes and 1/4,000. 1/8,000, 1/16,000 and 1/32,000 for the trough concentration test tubes. The Staphylococcus aureus (ATCC 29213) was also used as the standard test microorganism. The results showed that this organism exhibited a sensitivity to oxytetracycline hydrochloride at an MIC of 1 mcg/ml. According to the methodology outlined above, the initial peak concentrations of oxytetracycline hydrochloride in saliva were calculated to be 400 mg/ml and 800 mg/ml, and trough concentrations to be 8 mg/ml and 8 mg/ml in these two experiments.

In the medical literature, it has been reported that after an intravenous injection of 200 mg of tetracyclines, the average peak blood level usually reaches 4 mcg/ml. Intravenous injections of larger doses of tetracyclines are not recommended because of undesirable side-effects and complications. When the antibiotic troche of this invention is made of 50 mg of oxytetracycline hydrochloride, which cannot be safely injected in a single large dose, the advantage is remarkable. The trough and peak concentrations are about 2,000 to 100,000 times the peak blood level usually quoted in the medical literature. The inventor believes that this supratherapeutic level of antibiotics delivered directly over the lesion is one of the reasons for the success in using this dry dosage form of medication to treat canker sores.

Example III

TABLE 3

Production and Use of Penicillin/Magnesium Stearate Powder

| Compound | |
|---|---|
| Penicillin G or penicillin V potassium salt (80,000 Units) | 5000 mg |
| Magnesium stearate | 80 mg |
| Stearic acid | 60 mg |
| Lactose | 750 mg |
| Starch | 110 mg |
| Total weight | 6000 mg |

Table 3 shows the ingredients combined to make the penicillin/magnesium stearate powder of this invention. The above ingredients are in fine powder and mixed. An aliquot of 60 mg of the powder suspended in 2 ml of double-distilled water should yield a neutral acidity of pH 7.0±0.2, and should not cause desquamative injuries or erosion when applied to a localized spot of about 5 mm in diameter on an intact oral mucosa.

This formula is generally useful for children who may not be able to use the penicillin troches according to the directions given in Example I. Instead, an applicator (such as, for instance, a small easily opened packet) or an adult's finger will be used to apply the medicinal powder in the amount of 30 to 60 mg directly to the canker ulcer four times a day after meals and drinking.

If there are multiple canker ulcers in the mouth and are located far apart from one another, one dose of powder is required for the treatment of each ulcer. The patient is not given any food or drink for one hour. If the ulcer does not show any sign of healing in four days, the physician should pursue further investigation for diseases other than canker ulcers.

REFERENCES

International Pharmacopoeia, Vol I, II, (Eds. Osol A and Farrar G E), pp. 1007–1008. J. B. Lippincott Co., Philadelphia, 1955.

Oral Pathology, (Eds. Thomas K H and Goldman H M), p. 1068. The C. V. Mosby Co., St. Louis, 1960.

The Use of Antibiotics, (Eds. Kucers A and Bennett N), pp.16–18. J. B. Lippincott, Philadelphia, 1987.

Gastrointestinal Disease, Pathophysiology/Diagnosis/Management, (Eds. Sleisenger M H and Fordtran J S), p. 273. W. B. Saunders Co., Philadelphia, 1993.

Nelson Textbook of Pediatrics, (Behrman R E, Kliegman R M, and A M), p. 1889. W. B. Saunders Co., Philadelphia, 1996.

The Pharmacological Basis of Therapeutics, (Eds. Gilman A G, Goodman L S, Gilman A), p.1136. Macmillan Publishing Co., New York, 1980.

Merck manual of Diagnosis and Therapy, (Eds. Berkow R and Talbott J H), p. 1667, Merck & CO., Inc., Rahway, N.J., 1977.

J. Clin. Invest. (1995), 95(1): 227–233.

Kitasato Arch. Exp. Med. (1991), 64(4):263–269.

All supporting books cited in this specification are incorporated herein by reference in their entirety.

While the present invention has been described in connection with what is presently considered to be practical and preferred embodiments, it is understood that the present invention is not limited or restricted to the disclosed embodiments but, on the contrary, is intended to cover various modifications and equivalent arrangements included within the spirit and scope of the appended claims.

Thus, it is to be understood that variations in the described invention will be obvious to those skilled in the art without departing from the novel aspects of the present invention and such variations are intended to come within the scope of the claims.

What is claimed is:

1. A method of treating shallow apthous ulcers in the oral mucosa comprising directly topically administering in dry form a troche or a powder consisting essentially of a dry dosage of an antibiotic selected from the group consisting of penicillins, beta-lactam antibiotics, tetracyclines, aminoglycosides, cephalosporins, macrolides, vancomycin, bacitracin, chloramphenicol and their salts and mixtures thereof;

wherein the troche or powder delivers directly to the ulcer a dosage concentration level of the antibiotic which is substantially higher in comparison to dosage concentrations levels achieved if the antibiotic is delivered to the ulcer through blood by conventional gastrointestinal absorption, intramuscular or intravenous injection of the antibiotic.

2. The method according to claim 1, wherein antibiotic activity is maintained topically on the ulcer for about 1 hour.

3. The method according to claim 1, wherein the troche or powder, when dissolved in saliva at the site of the ulcer, at peak level directly delivers at least about 400 mg antibiotic per 1 ml of saliva.

4. The method according to claim 1 or claim 3, wherein the troche or powder, when dissolved in saliva at the site of the ulcer, maintains an antibiotic activity of at least about 2.5 mg antibiotic per 1 ml of saliva for at least about 1 hour.

5. The method according to claim 1, wherein the troche or powder, when directly applied to the aphthous ulcer, dissolves in saliva within about 5 to about 15 minutes.

6. The method according to claim 1, wherein the dry dosage is in the form of a troche.

7. The method according to claim 1, wherein the amount of antibiotic in the troche or powder is about 50 mg.

8. The method according to claim 1, wherein the antibiotic is a penicillin or a tetracycline, or a mixture thereof.

9. The method according to claim 1, wherein the antibiotic is penicillin and the initial peak concentration of penicillin in saliva at the site of the ulcer is about 800,000 Units per 1 ml saliva.

10. The method according to claim 9, wherein the local trough concentration of penicillin in saliva at the site of the ulcer is about 4,000 Units per 1 ml saliva for about 1 hour.

11. The method according to claim 1, wherein the antibiotic is oxytetracycline hydrochloride and the initial peak concentration of oxytetracycline hydrochloride in saliva at the site of the ulcer is between about 400–800 mg per 1 ml saliva.

12. The method according to claim 11, wherein the local trough concentration of oxytetracycline hydrochloride in saliva at the site of the ulcer is about 8 mg per 1 ml saliva for about 1 hour.

13. A method of treating shallow aphthous ulcers in the oral mucosa comprising directly topically administering a troche or a powder consisting essentially of a dry dosage of an antibiotic selected from the group consisting of penicillins, beta-lactam antibiotics, tetracyclines, aminoglycosides, cephalosporins, macrolides, vancomycin, bacitracin, chloramphenicol and their salts and mixtures thereof, and an effective amount of a salt or oxide of a polyvalent metal compound selected from the group consisting of magnesium, zinc, calcium, aluminum bismuth, titanium and copper and mixtures thereof;

wherein the troche or powder delivers directly to the ulcer a dosage concentration level of the antibiotic which is substantially higher in comparison to dosage concentrations levels achieved if the antibiotic is delivered to the ulcer through blood by conventional gastrointestinal absorption, intramuscular or intravenous injection of the antibiotic.

14. The method according to claim 13, wherein the polyvalent metal compound is delivered in a concentration sufficiently high that, when the troche or powder is dissolved in saliva at the site of the ulcer, it forms a protective barrier over the ulcer.

15. The method according to claim 13, wherein the polyvalent metal compound is delivered to the site of the ulcer in a concentration of between about 2–50 mg per 1 ml of saliva, when the troche or powder is dissolved in saliva at the site of the ulcer.

16. The method according to claim 15, wherein the concentration of the polyvalent metal compound delivered to the site of the ulcer is about 10 mg per 1 ml of saliva.

17. The method according to claim 13, wherein the amount of polyvalent metal compound in the troche or powder is between about 0.2–5 mg.

18. The method according to claim 13, wherein the polyvalent metal compound is magnesium stearate.

19. The method according to claim 13, wherein the antibiotic is a penicillin and the polyvalent metal compound is magnesium stearate.

20. The method according to claim 19, wherein the amount of penicillin in the troche or powder is about 50 mg and the amount of magnesium stearate is about 1.0 mg.

21. The method according to claim 13, wherein the antibiotic is a tetracycline and the polyvalent metal compound is magnesium stearate.

22. The method according to claim 21, wherein the amount of tetracycline in the troche or powder is about 50 mg and the amount of magnesium stearate is about 1.0 mg.

23. A dry topical medicament for treating shallow apthhous ulcers in the oral mucosa consisting essentially of a troche or a powder consisting essentially of about 10–200 mg of an antibiotic selected from the group consisting of penicillins, beta-lactam antibiotics, tetracyclines, aminoglycosides, cephalosporins, macrolides, vancomycin, bacitracin, chloramphenicol and their salts and mixtures thereof;
wherein the troche or powder delivers directly to the ulcer a dosage concentration level of the antibiotic which is substantially higher in comparison to dosage concentrations levels achieved if the antibiotic is delivered to the ulcer through blood by conventional gastrointestinal absorption, intramuscular or intravenous injection of the antibiotic.

24. The medicament according to claim 23, wherein antibiotic activity is maintained topically on the ulcer for about 1 hour.

25. The medicament according to claim 23, wherein the troche or powder, when dissolved in saliva at the site of the ulcer, at peak level directly delivers at least about 400 mg antibiotic per 1 ml of saliva.

26. The medicament according to claim 23 or claim 25, wherein the troche or powder, when dissolved in saliva at the site of the ulcer, maintains an antibiotic activity of at least about 2.5 mg antibiotic per 1 ml of saliva for at least about 1 hour.

27. The medicament according to claim 23, wherein the troche or powder, when directly applied to the aphthous ulcer, dissolves in saliva within about 5 to about 15 minutes.

28. The medicament according to claim 23, wherein the dry dosage is in the form of a troche.

29. The medicament according to claim 23, wherein the amount of antibiotic in the troche or powder is about 50 mg.

30. The medicament according to claim 23, wherein the antibiotic is a penicillin or a tetracycline, or a mixture thereof.

31. The medicament according to claim 23, wherein the antibiotic is a penicillin and the initial peak concentration of penicillin in saliva at the site of the ulcer is about 800,000 Units per 1 ml saliva.

32. The medicament according to claim 31, wherein the local trough concentration of penicillin in saliva at the site of the ulcer is about 4,000 Units per 1 ml saliva for about 1 hour.

33. The medicament according to claim 23, wherein the antibiotic is oxytetracycline hydrochloride and the initial peak concentration of oxytetracycline hydrochloride in saliva at the site of the ulcer is between about 400–800 mg per 1 ml saliva.

34. The medicament according to claim 33, wherein the local trough concentration of oxytetracycline hydrochloride in saliva at the site of the ulcer is about 8 mg per 1 ml saliva for about 1 hour.

35. A dry topical medicament for treating shallow apthhous ulcers in the oral mucosa comprising a troche or a powder consisting essentially of about 10–200 mg of an antibiotic selected from the group consisting of penicillins, beta-lactam antibiotics, tetracyclines, aminoglycosides, cephalosporins, macrolides, vancomycin, bacitracin, chloramphenical and their salts and mixtures thereof, and an effective amount of a salt or oxide of a polyvalent metal compound selected from the group consisting of magnesium, zinc, calcium, aluminum, bismuth, titanium and copper and mixtures thereof;
wherein the troche or powder delivers directly to the ulcer a dosage concentration level of the antibiotic which is substantially higher in comparison to dosage concentrations levels achieved if the antibiotic is delivered to the ulcer through blood by conventional gastrointestinal absorption, intramuscular or intravenous injection of the antibiotic.

36. The medicament according to claim 35, wherein the polyvalent metal compound is delivered in a concentration sufficiently high that, when the troche or powder is dissolved in saliva at the site of the ulcer, it forms a protective barrier over the ulcer.

37. The medicament according to claim 35, wherein the polyvalent metal compound is delivered to the site of the ulcer in a concentration of between about 2–50 mg per 1 ml of saliva, when the troche or powder is dissolved in saliva at the site of the ulcer.

38. The medicament according to claim 37, wherein the concentration of the polyvalent metal compound delivered to the site of the ulcer is about 10 mg per 1 ml of saliva.

39. The medicament according to claim 35, wherein the amount of polyvalent metal compound in the troche or powder is between about 0.2–5 mg.

40. The medicament according to claim 35, wherein the polyvalent metal compound is magnesium stearate.

41. The medicament according to claim 35, wherein the antibiotic is a penicillin and the polyvalent metal compound is magnesium stearate.

42. The medicament according to claim 41, wherein the amount of penicillin in the troche or powder is about 50 mg and the amount of magnesium stearate is about 1.0 mg.

43. The medicament according to claim 35, wherein the antibiotic is a tetracycline and the polyvalent metal compound is magnesium stearate.

44. The medicament according to claim 43, wherein the amount of tetracycline in the troche or powder is about 50 mg and the amount of magnesium stearate is about 1.0 mg.

* * * * *